United States Patent
Martin et al.

(10) Patent No.: US 9,700,404 B2
(45) Date of Patent: Jul. 11, 2017

(54) TISSUE EXPANDER IMPLANT WITH SELF-SEALING SAFETY PATCH

(71) Applicant: Ethicon, Inc., Somerville, NJ (US)

(72) Inventors: Alisha M. Martin, Dallas, TX (US); Anita Falcon, Bedford, TX (US); Cathy O. Glines, Coppell, TX (US); Philip M. Steele, Allen, TX (US)

(73) Assignee: ETHICON, INC., Somerville, NJ (US)

( * ) Notice: Subject to any disclaimer, the term of this patent is extended or adjusted under 35 U.S.C. 154(b) by 167 days.

(21) Appl. No.: 13/830,547

(22) Filed: Mar. 14, 2013

(65) Prior Publication Data

US 2014/0277440 A1  Sep. 18, 2014

(51) Int. Cl.
*A61F 2/12* (2006.01)
*B29C 43/24* (2006.01)
*A61B 90/00* (2016.01)

(52) U.S. Cl.
CPC .............. *A61F 2/12* (2013.01); *A61B 90/02* (2016.02); *B29C 43/24* (2013.01); *A61F 2250/0003* (2013.01); *A61F 2250/0069* (2013.01)

(58) Field of Classification Search
CPC .............. A61F 2/52; A61F 2002/523; A61F 13/00029; A61F 2250/0003; A61F 2250/0069; A61F 2/12; A61F 2/441; A61F 2/442; A61M 29/02; A61B 90/02; A61B 17/7097; A61B 17/8855
USPC .......... 623/7, 8, 17.12, 23.67, 23.68, 23.72; 606/191, 192, 193, 194, 195; 450/38
See application file for complete search history.

(56) References Cited

U.S. PATENT DOCUMENTS

| | | | |
|---|---|---|---|
| 3,020,260 A | 2/1962 | Nelson | |
| 3,600,718 A | 8/1971 | Boone | |
| 3,919,724 A | 11/1975 | Sanders et al. | |
| 4,455,691 A | 6/1984 | Van Aken Redinger et al. | |
| 4,592,755 A | 6/1986 | Penton et al. | |
| 4,662,883 A | 5/1987 | Bell et al. | |
| 4,671,255 A * | 6/1987 | Dubrul et al. | 128/899 |
| 4,889,744 A * | 12/1989 | Quaid | 427/2.24 |

(Continued)

FOREIGN PATENT DOCUMENTS

WO    WO 2011/097292 A1    8/2011

OTHER PUBLICATIONS

Siltex Contour Profile Breast Tissue Expanders, http://www.mentorwwllc.com/pdfs-global/breast/EN/adcards/CPX.pdf, Jul. 2007, 2 pp.

*Primary Examiner* — David Isabella
*Assistant Examiner* — Rokhaya Diop

(57) ABSTRACT

Disclosed is a self-sealing patch for use with a tissue expander implant. The self-sealing patch serves as protection for the tissue expander against a hypodermic needle inadvertently missing a fluid injection port thereof by sealing a puncture through the patch. The patch includes a first sheet having a first sheet perimeter, a second sheet having a second sheet perimeter attached to the first sheet perimeter to form a pocket between the first sheet and the second sheet. Material is disposed within the pocket, where the material is hydrophobic material having a viscosity high enough that the material is prevented from flowing outside the pocket when either the first or second sheet is punctured with a hypodermic needle but low enough that the material flows to close a track made by a hypodermic needle puncturing the first or second sheet.

20 Claims, 3 Drawing Sheets

(56) References Cited

U.S. PATENT DOCUMENTS

| | | |
|---|---|---|
| 4,944,749 A | 7/1990 | Becker |
| 5,019,101 A | 5/1991 | Purkait et al. |
| 5,022,942 A | 6/1991 | Yan et al. |
| 5,066,303 A | 11/1991 | Bark et al. |
| 5,133,753 A | 7/1992 | Bark et al. |
| 5,456,716 A | 10/1995 | Iversen et al. |
| 6,074,421 A | 6/2000 | Murphy |
| 6,371,984 B1 | 4/2002 | Van Dyke et al. |
| 6,588,432 B1 | 7/2003 | Rehder et al. |
| 6,743,254 B2 | 6/2004 | Guest et al. |
| 6,752,965 B2 | 6/2004 | Levy |
| 6,790,213 B2 * | 9/2004 | Cherok et al. ............... 606/151 |
| 7,789,911 B2 | 9/2010 | Hamilton |
| 8,070,809 B2 | 12/2011 | Schuessler |
| 2003/0149481 A1* | 8/2003 | Guest et al. ...................... 623/8 |
| 2007/0135913 A1* | 6/2007 | Moaddeb et al. ........... 623/2.37 |
| 2009/0259313 A1* | 10/2009 | Elsner et al. .............. 623/14.12 |
| 2010/0049316 A1 | 2/2010 | Schuessler |
| 2010/0228347 A1 | 9/2010 | Schuessler |
| 2011/0160854 A1 | 6/2011 | Berg et al. |
| 2011/0270391 A1* | 11/2011 | Chitre et al. ...................... 623/8 |
| 2011/0288639 A1 | 11/2011 | Trilokekar et al. |
| 2012/0123537 A1 | 5/2012 | Manesis et al. |

* cited by examiner

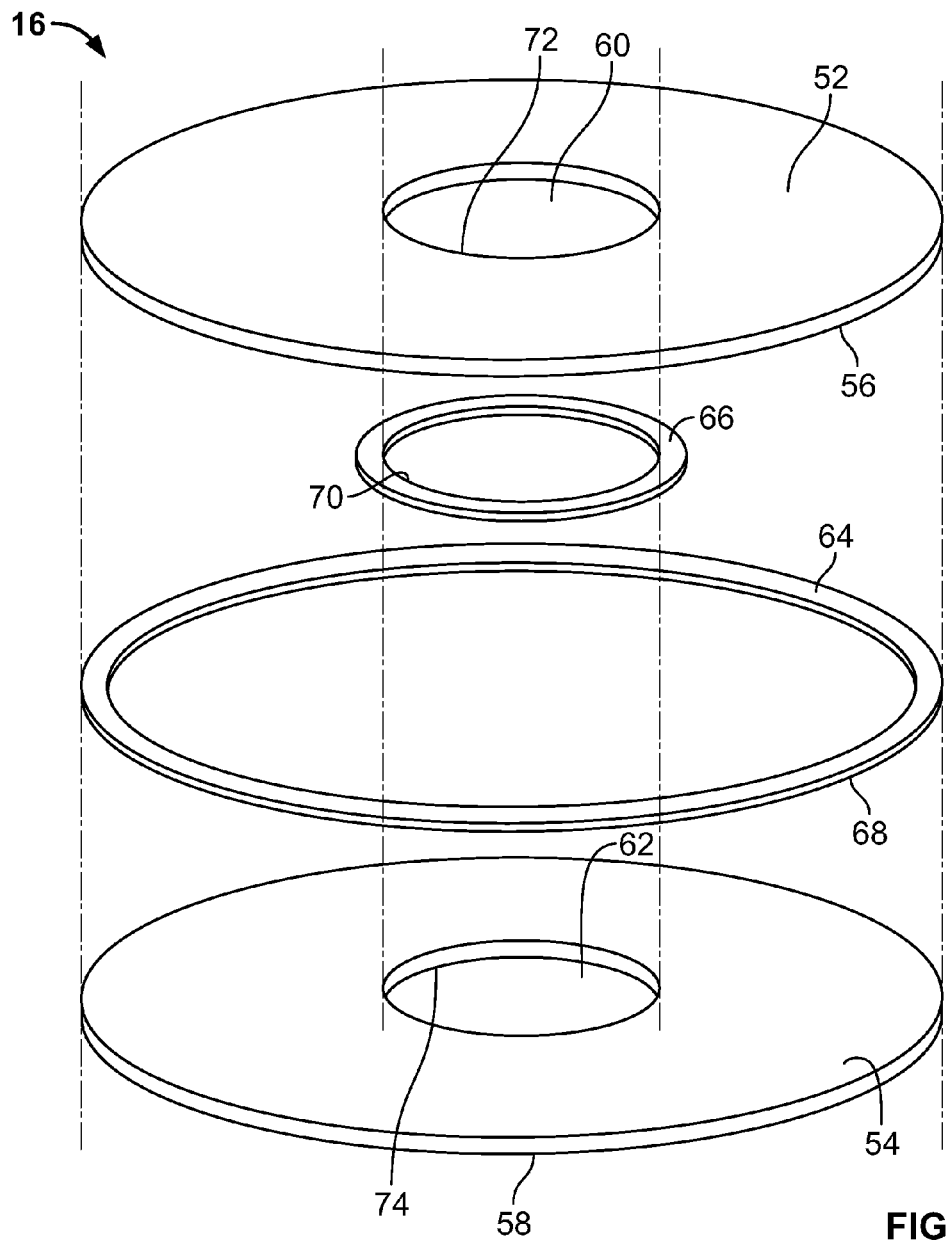
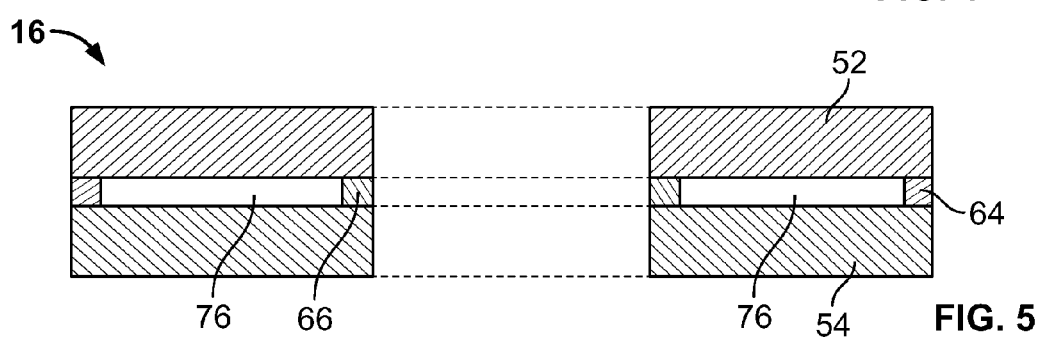

US 9,700,404 B2

TISSUE EXPANDER IMPLANT WITH SELF-SEALING SAFETY PATCH

BACKGROUND OF THE INVENTION

The present invention relates to implantable tissue expanders and prostheses. Although the tissue expanders may be used in other areas of the body, one specific application of the inventive subject matter are implantable mammary soft tissue expanders.

Tissue expanders are devices that are implanted beneath the skin and then gradually inflated to stretch the overlying tissue. Expanders are commonly used either to create a pocket for receiving a permanent prosthesis or to generate an increased skin surface area in anticipation of the new skin being utilized for grafting or reconstruction.

Conventional implantable tissue expanders are formed of a silicone polymer shell. After implantation, a fluid such as saline is periodically injected into the expander for expansion. Between injections, the surrounding skin is permitted to stretch and grow to create the increased skin surface.

The saline or other fluid may also be withdrawn from the expander to reduce its volume. In addition, the shell can be partially filled with fluid or gel prior to implantation.

Typically, a tissue expander will be provided with an injection dome, for example, a dome comprising a septum that can be pierced with a hypodermic needle for the introduction of fluid directly into the expander or withdrawal of fluid directly from the expander. However, it can be difficult to accurately locate the injection dome through the overlying tissue. If the injection dome is missed and the needle punctures the shell of the tissue expander adjacent to the injection dome, the expander can leak. Most often, any leaking requires that the expander be removed and replaced.

This problem can be addressed by providing an injection dome that is remote from the tissue expander but is in fluid communication with the expander. Other solutions include eliminating the need for an injection site altogether by forming the expander with a self-sealing shell that can be pierced with a hypodermic needle at any location for the purpose of adding fluid to the shell.

Still further solutions include providing an injection dome surrounded by a self-sealing member that reduces the risk of causing a leak in the tissue expander in the event that the hypodermic needle used to fill the expander accidentally misses the injection dome. Such an arrangement reduces the frequency with which expanders require removal due to leakage caused by inadvertent punctures. It is this type of arrangement that is the focus of the present invention, which draws on the teachings of U.S. Pat. No. 6,743,254, the disclosure of which is hereby incorporated by reference herein.

BRIEF SUMMARY OF THE INVENTION

Although well received, systems and methods of the types described above are not ideal. Particularly with respect to injection domes surrounded by self-sealing members, it has been found that the conventional self-sealing members are stiff and may be perceived as being uncomfortable for some patients. It has also been found that the injection domes are difficult for medical staff to locate.

The present invention therefore provides for a tissue expander having an injection dome surrounded by a self-sealing member with improved features. These features include self-sealing patches that are more flexible and softer than conventional patches. The features also include the removal of a palpitation ring and incorporation of a stronger locating magnet that aids in medical staff identifying the proper location for the filling hypodermic needle.

In accordance with one aspect of the invention, there is provided a tissue expander comprising an outer shell configured to retain a fluid; an injection dome comprising a self-sealing septum region arranged through the outer shell, the injection dome adapted to accept a hypodermic needle to fill the outer shell with fluid; a self-sealing patch arranged around the injection dome and along the outer shell, the self-sealing patch comprising a first sheet having a first sheet perimeter and forming a first central opening; a second sheet having a second sheet perimeter and forming a second central opening; an outer washer arranged between the first and second sheets at the first sheet perimeter and the second sheet perimeter; and a second washer arranged between the first and second sheets at the first central opening and the second central opening. The first sheet and the second sheet bound an annular space formed between the outer washer and the inner washer, the annular space filled with a self-sealing material.

The self-sealing patch may be arranged on an inner surface of the outer shell.

The injection dome may further comprise a magnetized area of between 650 gauss and 13,000 gauss at 5 mm.

The self-sealing material in the annular space may be hydrophobic material having a viscosity high enough that the material is prevented from flowing outside the pocket when either the first or second sheet is punctured with a hypodermic needle but low enough that the material flows to close a track made by a hypodermic needle puncturing the first or second sheet. Such hydrophobic material may be one of a liquid silicone rubber, cohesive gel, sensitive gel, or memory gel.

In accordance with a further aspect of the invention, a self-sealing patch for use with a tissue expander implant comprises a first sheet having a first sheet perimeter; a second sheet having a second sheet perimeter attached to the first sheet perimeter to form a pocket between the first sheet and the second sheet; material disposed within the pocket, wherein the material is hydrophobic material having a viscosity high enough that the material is prevented from flowing outside the pocket when either the first or second sheet is punctured with a hypodermic needle but low enough that the material flows to close a track made by a hypodermic needle puncturing the first or second sheet.

The hydrophobic material may be one of a liquid silicone rubber, cohesive gel, sensitive gel, or memory gel.

The first sheet may be formed from a low bleed silicone patch material comprising three layers having an overall thickness of between approximately 0.014" to 0.090". The first sheet may be formed from a material comprising a polydiphenylsiloxane layer between polydimethysiloxane layers.

The first sheet may be formed from a material made from vulcanized polydimethylsiloxane with a thickness of approximately 0.004" to 0.010".

The first sheet may be formed from a material made from unvulcanized polydimethylsiloxane with a thickness of approximately 0.004" to 0.010".

The first sheet may be formed from polyethylene terephthalate reinforced vulcanized polydimethylsiloxane with a thickness of approximately 0.013" to 0.018".

The first sheet may be reinforced with a Polyethylene terephthalate (PET) mesh.

The first sheet may be reinforced with a third sheet of para-aramid synthetic fibers.

The self-sealing patch may further comprise an outer washer disposed between the first sheet perimeter and the second sheet perimeter to attach the first sheet perimeter to the second sheet perimeter.

The self-sealing patch may further comprise a central opening within the first sheet perimeter and the second sheet perimeter, the central opening formed by a washer located between the first sheet and the second sheet.

In accordance with a still further aspect of the invention, a method of forming a self-sealing patch for use in a tissue expander implant comprises, in no particular order, forming a first sheet by pressing silicone in a calendaring process; partially curing the first sheet; forming a second sheet by pressing silicone material in a rolling machine; fully curing the second sheet; attaching the first sheet to the second sheet with silicone washers to form an annular space; and filling the annular space with a self-sealing material.

The method may further comprise reinforcing the first sheet with a PET mesh.

The step of forming the second sheet may include pressing the silicone material with a PET mesh.

The step of partially curing the first sheet may leave a first side of the first sheet tacky.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof, will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

With respect to the drawings,

FIG. 4 is an exploded view of the safety patch of FIG. 1; and,

FIG. 5 is a cross-sectional view of the safety patch of FIG. 1.

DETAILED DESCRIPTION

Figures 1, 2:
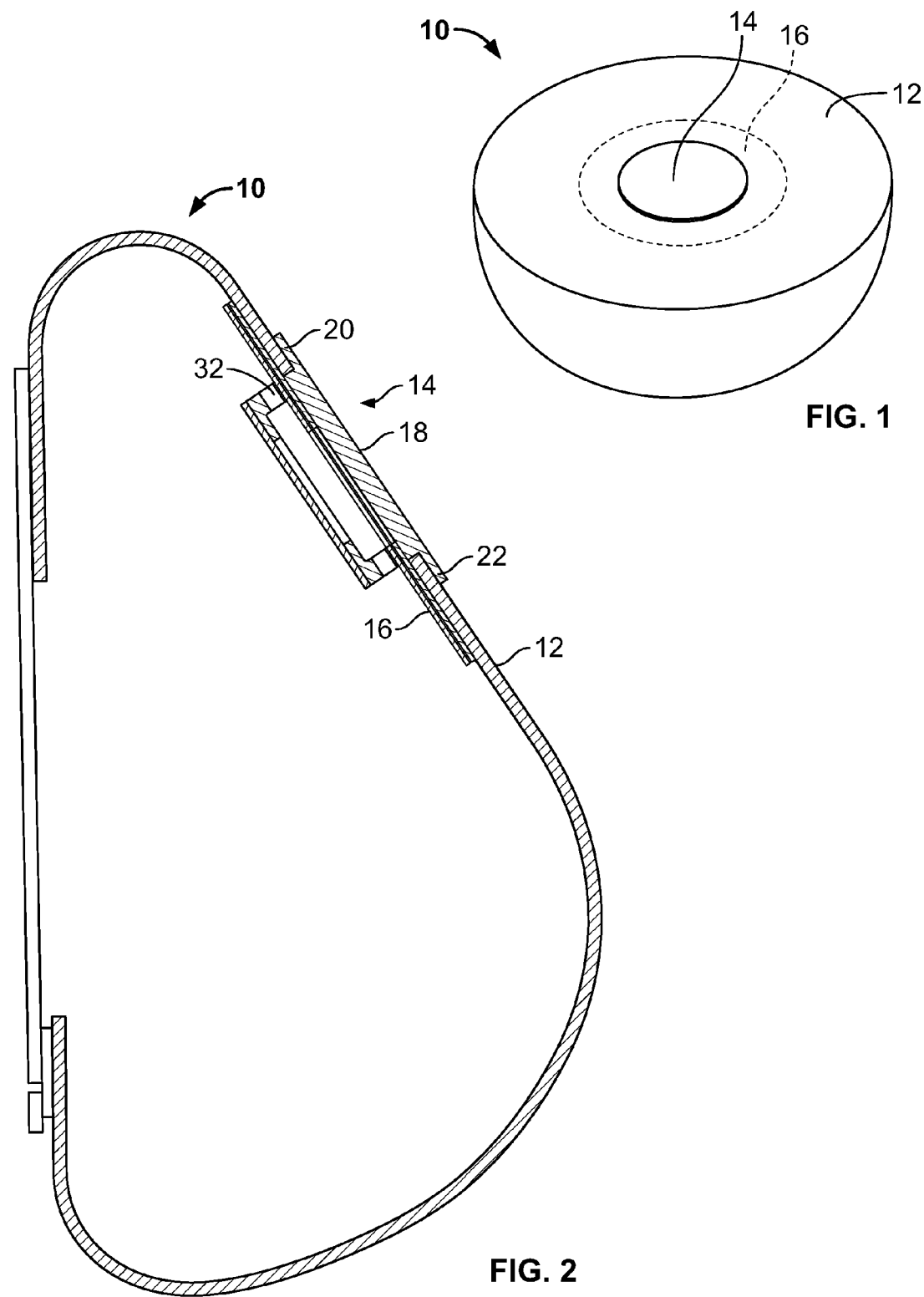
FIG. 1 is a perspective view of an exemplary tissue expander implant with self-sealing safety patch.
FIG. 2 is a cross-sectional view of the tissue expander of FIG. 1.

In the following are described the preferred embodiments of the tissue expander implant with self-sealing safety patch of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose. Where like elements have been depicted in multiple embodiments, identical reference numerals have been used in the multiple embodiments for ease of understanding.

As discussed above, the invention features a tissue expander implant with self-sealing safety patch. The self-sealing safety patch surrounds an injection dome to aid with sealing of the tissue expander implant upon inadvertent placement of a filling hypodermic needle outside of the injection dome.

Although the tissue expander with self-sealing safety patch of the present invention may be utilized for any tissue expander, the following description is provided for its use in a mammary tissue expander. Typically, such an expander will be placed in the body submuscularly, primarily beneath the pectoralis major, pectoralis minor, and/or serratus anterior, subcutaneously, or subglandularly.

FIG. 1 depicts a perspective view of a mammary tissue expander in accordance with one embodiment of the present invention. As shown, the expander 10 includes an outer shell 12, preferably made of a cross-linked silicone elastomer. The outer shell 12 includes an injection dome 14. A fluid dispensing device, such as an injection syringe (not shown), is used to add or remove fluid from the outer shell 12 through the injection dome 14 to adjust the shell's volume. The present invention protects the integrity of the expander 10 by providing a safeguard against a syringe failing to penetrate the injection dome 14, but rather entering the outer shell 12 in the immediate area adjacent the injection dome 14. It does so by providing a self-sealing safety patch 16 in the immediate vicinity surrounding the injection dome 14.

Typically the self-sealing safety patch 16 will be oval or round. It will be appreciated that the size of the self-sealing safety patch 16 may be scaled depending on, and in relation to, the size of the outer shell 12.

FIG. 2 depicts a cross-sectional view of the mammary tissue expander 10 of FIG. 1. Again, the mammary tissue expander 10 includes an outer shell 12 with an injection dome 14. Also shown is the self-sealing safety patch 16 formed around the injection dome 14.

Figure 3:
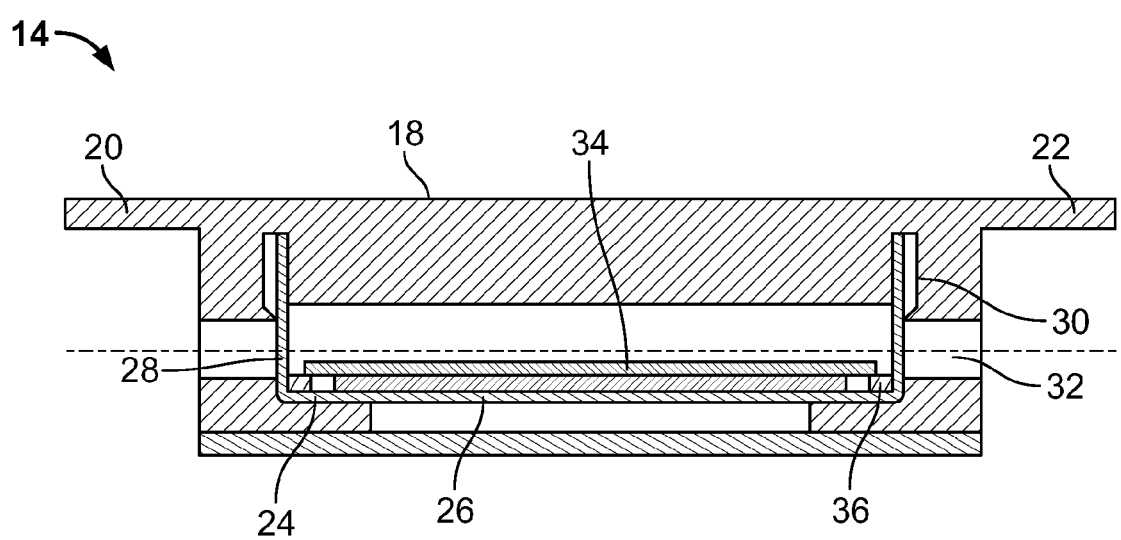
FIG. 3 is a cross-sectional view of the injection port of the tissue expander of FIG. 1.

FIG. 3 is a cross-sectional view of the injection dome 14 depicting additional details thereof. The function of the injection dome 14 is to allow controlled introduction and removal of fluid to and from the tissue expander 10. Generally, this is accomplished through use of a hypodermic needle (not shown) that pierces a selected region of the injection dome 14, e.g., septum region 18 formed of elastomeric material. The injection dome 14 is fitted into an opening in the outer shell 12, for example at a portion which is intended to face the skin of the patient to be expanded. The casing 20 of the injection dome is typically formed of an elastomeric material.

The septum region 18 of the casing 20 is preferably located at the central region of the upper surface of the casing. The septum region 18 is self-sealing, preventing the leaking of fluid from the implant 10 after removal of the hypodermic needle from the injection dome. A flange 22 extends around the upper edge of the dome casing 20. As shown more clearly in FIG. 2, the flange 22 overhangs the shell 12, which is partially sandwiched between the flange and the self-sealing safety patch 16. As the flange 22 rests against the outer surface of the shell 12, it provides a surface for securely attaching the assembled injection dome 14 to the shell.

In order to prevent accidental puncture of the shell 12 through the injection dome 14 itself, the injection dome is equipped with a needle guard 24 in the form of a metal cup forming a base portion 26 and a rim portion 28. The rim portion 28 is fitted into to an annular slot 30 in the underside of the dome casing 20. When the needle guard 24 is inserted into the slot 30 in the injection dome 14, compressive force is exerted on the elastomeric material of the septum region 18 of the injection dome 14. As a result of these forces, the septum region 18 of the injection dome 14, is self-sealing.

Openings 32 in the rim portion 28 of the needle guard 24 allow fluid to pass to the interior of the shell 12.

A needle damper 34, preferably formed of a resilient material, e.g., polysulfone, is positioned on top of the base 26 of the needle guard 24 to prevent damage to the hypodermic needle tip should the needle be insert so far as to actually strike the needle guard. It is prudent to reduce the risk of damage to the hypodermic needle because a bent tip could tear a non-repairable hole that compromises the self-sealing capability in the septum region 18 upon withdrawal of the needle from the injection dome 14. The needle damper 34 is preferably adhesively fastened to the needle guard 24.

The injection dome 14 can be modified in various ways to help the medical professional accurately locate the septum region 18 beneath the skin of the recipient. For example, the dome can include a raised "palpation" ridge (not shown) that encircles the actual septum region 18. The injection dome can also, or alternatively, be provided with a magnet, e.g., a magnet 36 attached to the needle guard 24, that allows the injection dome 14 to be located by passing a device capable of locating a magnetic field over the patient's skin. Unlike prior art magnets that are generally in the range of 414 gauss at 5 mm, magnets 36 of the present invention are preferably 650 gauss or greater at 5 mm. Preferably, these magnets are less than 13,000 gauss at 5 mm. This provides a stronger magnetic field for the medical professional to locate the septum than previously known. This is useful particularly where there are no "palpation" ridges in the injection dome 14.

The outer shell 12 of the tissue expander of the invention can have any desired shape and any thickness that is suitable for the purpose of the particular expander. The shell may be single lumen or multi-lumen and is commonly formed of a biocompatible elastomer, e.g., silicone. Dip molding using an appropriately sized and shaped mandrel can be used to form the outer shell 12. The mandrel is dipped into silicone dispersion and then removed to allow partial cure or solvent evaporation. The process is generally repeated several times. Once the outer shell 12 has been formed it is removed from the mandrel. (Other methods such as injection molding or spraying may also be used to form the shell.)

This dip molding process results in the formation of a partial shell that has an opening, e.g., a circular hole (patch hole) on its face. The self-sealing patch 16 is applied to the inner or outer surface of the outer shell 12, e.g., in the region that will surround the injection dome 14. The injection dome 14 is installed and the patch hole is subsequently covered with a patch that seals the hole, thus forming a complete, fluid impervious shell. The patch is attached to the partial shell using silicone rubber or other similar biocompatible adhesive. The completed shell can either be non-filled or partially pre-filled. After implantation, the expander 10 is intraoperatively filled through the septum region 18 with saline, gel, foam, or combinations of these materials or other suitable materials known in the art to gradually expand the tissue expander to the desired dimensions.

FIG. 4 depicts an exploded view of a self-sealing patch 16 in accordance with the present invention. As shown, the self-sealing patch is comprised of four major components. At one end of the self-sealing patch 16 is a first sheet 52 and at a second end of the self-sealing patch is a second sheet 54. The first sheet 52 includes a first perimeter 56 around the exterior circumference thereof while the second sheet 54 includes a second perimeter 58 around its exterior circumference. Each of the first sheet 52 and second sheet 54 includes an aperture region 60, 62 respectively, formed generally in each sheet's central portion.

Between the first sheet 52 and second sheet 54 are an outer washer 64 and an inner washer 66. The outer washer 64 has an outer perimeter 68 corresponding to the first and second perimeters 56, 58 and is preferably approximately 5 mm thick (measured between its inner and outer diameters). The inner washer 66 includes an inner perimeter 70 corresponding to the edges 72, 74 of the aperture regions 60, 62 and is also approximately 3 mm thick.

When pressed together, the first sheet 52 and second sheet 54 capture the washers 64, 66 to create an annular space 76, or pocket (see FIG. 5), between the four elements. This annular space 76 is preferably filled with a substance that will self-seal, for example a substance that is hydrophobic having a viscosity high enough that the material is prevented from flowing outside the annular space when either the first or second sheet is punctured with a hypodermic needle but low enough that the material flows to close a track made by a hypodermic needle puncturing the first or second sheet. Typically this property is measured as a function of stiffness/firmness and cohesion, with a penetration value of approximately 3-10 mm. Hydrophobic materials are chosen because hydrophilic materials may open the tissue expander to greater osmotic exchange with the local environment than a hydrophobic material.

Substances suitable for filling the annular space 76 include:

Liquid silicone rubber (LSR).

Cohesive gel. It is noted that cohesive gel is available commercially as manufactured at least by Mentor Worldwide LLC.

Sensitive gel. It is noted that sensitive gel is available commercially as manufactured at least by Mentor Worldwide LLC.

Memorygel® as produced by Mentor Worldwide LLC. Memorygel® is a registered trademark of Mentor Worldwide LLC, 5425 Hollister Avenue, Santa Barbara, Calif. 93111.

Once the patch is filled, a small amount of silicone adhesive can be used to seal the entry point of the filling mechanism.

The first and second sheets 52, 54 of the patch 16 are preferably similarly sized oval sheets. It will be appreciated that the patch dimensions and the dimensions of each part can be scaled based on implant size and profile. Typically, the patch 16 will exceed the bounds of the injection dome 14 on each side of the injection dome.

The first and second sheets 52, 54 are each typically manufactured from matching materials, but can be formed from different combinations of materials. Among the suitable materials are:

Low bleed silicone patch material comprising three layers having an overall thickness of approximately 0.014" to 0.090".

Material that comprises a polydiphenylsiloxane layer between polydimethysiloxane layers.

Vulcanized or unvulcanized polydimethylsiloxane with a thickness of approximately 0.004" to 0.0192". A specific example of this arrangement is the use of NuSil® MED4750 silicone, which is a 1:1 blend of a two part system. Part A of the system contains a base polymer functionalized with vinyl groups and containing a platinum catalyst. Part B of the system contains the silyl hydride crosslinker. NuSil® is a registered trademark of Nusil Technology LLC, 1050 Cindy Lane, Carpinteria, Calif. 93013.

Additionally, any of the aforementioned materials may be reinforced with a Polyethylene terephthalate (PET) mesh.

The materials may also be reinforced with a sheet made from para-aramid synthetic fibers. With these reinforcements, the sheet thickness may rise to approximately 0.013" to 0.018" or greater.

In one particular example, the two sheets 52, 54 are made as follows. The first sheet 52, reinforced with a PET mesh, is made by pressing blended NuSil® 4750 silicone material in a calendaring process. This sheet is partially cured to leave one side tacky for attaching to the implant shell. The second sheet is made by pressing blended NuSil® 4750 silicone material along with a PET mesh on one side in a rolling machine. This PET sheet is fully cured.

The first and second sheets 52, 54 are attached to each other using the two washers 64, 66, which are formed from silicone. Washer 64, aligning with the first and second perimeters 56, 58 is 5 mm in width. The washer 64 is preferably formed from unvulcanized NuSil® MED 4750 material, but may also be formed from other materials such as 4735. The washer 66 aligned with the aperture regions 60, 62 is cut from unvulcanized sheeting preferably made from NuSil® MED 4750. The washer may also be formed from other materials such as 4375. The washers 64, 66 thereafter act to form a sealed annular space 76. The pocket is then filled with any of the suitable substances identified above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A tissue expander comprising:
    an outer shell configured to retain a fluid;
    an injection dome comprising a self-sealing septum region arranged through said outer shell, said injection dome adapted to accept a hypodermic needle to fill said outer shell with fluid;
    a self-sealing patch arranged around said injection dome and along said outer shell, said self-sealing patch consisting of:
    a first sheet having a first sheet outer perimeter and a first sheet inner edge defining a first sheet central opening;
    a second sheet having a second sheet outer perimeter aligned with said first sheet outer perimeter and a second sheet inner edge defining a second sheet central opening aligned with said first sheet central opening;
    an outer washer captured between said first and second sheets at said first sheet outer perimeter and said second sheet outer perimeter; and,
    an inner washer captured between said first and second sheets at said first sheet central opening and said second sheet central opening;
    wherein said first sheet and said second sheet are attached to one another using said outer and inner washers to form a sealed annular space between an inner perimeter of said outer washer and an outer perimeter of said inner washer, said sealed annular space being filled with a self-sealing material.

2. The tissue expander of claim 1, wherein said self-sealing patch is arranged on an inner surface of said outer shell.

3. The tissue expander of claim 1, wherein said injection dome further comprises a magnetized area of between 650 gauss and 13,000 gauss at 5 mm.

4. The tissue expander of claim 1, wherein said outer washer is in contact with said first and second sheets to form a first seal at said first and second sheet outer perimeters and said inner washer is in contact with said first and second sheets to form a second seal at said first and second sheet central openings, and wherein said self-sealing material in said sealed annular space is hydrophobic material having a viscosity high enough that said material is prevented from flowing outside said sealed annular space when either the first or second sheet is punctured with a hypodermic needle but low enough that said material flows to close a track made by a hypodermic needle puncturing said first or second sheet.

5. The tissue expander of claim 4, wherein said hydrophobic material is one of a liquid silicone rubber, cohesive gel, or sensitive gel.

6. The tissue expander of claim 1, wherein said first and second sheets are similarly sized oval sheets, wherein said outer washer is attached to said first and second sheets at said first sheet outer perimeter and said second sheet outer perimeter, and wherein said inner washer is attached to said first and second sheets at said first sheet central opening and said second sheet central opening.

7. The tissue expander of claim 1, wherein said outer and inner washers are ring shaped and spaced from one another, wherein said outer washer is larger than said inner washer, and wherein said inner washer has an inner perimeter that is aligned with said first sheet inner edge defining said first sheet opening and said second sheet inner edge defining said second sheet opening.

8. The tissue expander as claimed in claim 1, wherein there are no layers of fabric between first and second sheets.

9. A self-sealing patch for use with a tissue expander implant, the self-sealing patch comprising:
    a first sheet having a first sheet outer perimeter and a first sheet inner edge defining a first sheet central opening;
    a second sheet having a second sheet outer perimeter aligned with said first sheet outer perimeter and a second sheet inner edge defining a second sheet central opening aligned with said first sheet central opening;
    an outer washer captured between said first and second sheets at said first sheet outer perimeter and said second sheet outer perimeter;
    an inner washer captured between said first and second sheets at said first sheet central opening and said second sheet central opening;
    said first and second sheets being attached to one another using said outer and inner washers and an inner perimeter of said outer washer being spaced from an outer perimeter of said inner washer to form a sealed annular space between said first sheet, said second sheet, said outer washer, and said inner washer, wherein there are no layers of fabric between said first and second sheets;
    a material disposed within said sealed annular space, wherein said material is hydrophobic material having a viscosity high enough that said material is prevented from flowing outside said sealed annular space when either said first or second sheet is punctured with a hypodermic needle but low enough that said material flows to close a track made by a hypodermic needle puncturing said first or second sheet.

10. The self-sealing patch of claim 9, where said hydrophobic material is one of a liquid silicone rubber, cohesive gel, or sensitive gel.

11. The self-sealing patch of claim 9, wherein said first sheet is formed from a low bleed silicone patch material comprising three layers having an overall thickness between approximately 0.014" to 0.090".

12. The self-sealing patch of claim 9, wherein said first sheet is formed from a material comprising a polydiphenylsiloxane layer between polydimethylsiloxane layers.

13. The self-sealing patch of claim 9, wherein said first sheet is formed from a material made from vulcanized polydimethylsiloxane with a thickness of approximately 0.004" to 0.010".

14. The self-sealing patch of claim 9, wherein said first sheet is formed from a material made from unvulcanized polydimethylsiloxane with a thickness of approximately 0.004" to 0.010".

15. The self-sealing patch of claim 9, wherein said first sheet is formed from polyethylene terephthalate reinforced vulcanized polydimethylsiloxane with a thickness of approximately 0.013" to 0.018".

16. The self-sealing patch of claim 9, wherein said first sheet is reinforced with a Polyethylene terephthalate (PET) mesh.

17. The self-sealing patch of claim 9, wherein said first sheet is reinforced with a third sheet of para-aramid synthetic fibers.

18. The self-sealing patch of claim 9, further comprising a central opening aligned with said first sheet central opening and said second sheet central opening that is formed by an inner perimeter of said inner washer located between said first sheet and said second sheet, wherein said inner perimeter of said inner washer is aligned with both said first sheet inner edge defining said first sheet central opening and said second sheet inner edge defining said second sheet central opening.

19. The self-sealing patch of claim 9, wherein said outer washer is larger than said inner washer, and wherein said inner washer has an inner perimeter that is aligned with said first sheet inner edge defining said first sheet central opening and said second sheet inner edge defining said second sheet central opening.

20. The self-sealing patch of claim 9, wherein said outer and inner washers are ring shaped and spaced from one another, and wherein said inner washer has an inner perimeter that is aligned with said first sheet inner edge defining said first sheet central opening and said second sheet inner edge defining said second sheet central opening.

* * * * *